United States Patent
Sanderson et al.

(10) Patent No.: US 9,809,540 B2
(45) Date of Patent: Nov. 7, 2017

(54) HYDROBROMIDE SALT OF N-(4-CHLORO-2-HYDROXY-3-((3S)-3-PIPERIDINYLSULFONYL)PHENYL-N'-(3-FLUORO-2-METHYLPHENYL)UREA

(71) Applicant: GlaxoSmithKline Intellectual Property (No.2) Limited, Brentford, Middlesex (GB)

(72) Inventors: Francis Dominic Sanderson, Ware (GB); Sarah Mary Vallance, Stevenage (GB)

(73) Assignee: GLAXOSMITHKLINE INTELLECTUAL PROPERTY (NO.2) LIMITED (GB)

( * ) Notice: Subject to any disclaimer, the term of this patent is extended or adjusted under 35 U.S.C. 154(b) by 0 days.

(21) Appl. No.: 15/034,583

(22) PCT Filed: Nov. 11, 2014

(86) PCT No.: PCT/EP2014/074222
§ 371 (c)(1),
(2) Date: May 5, 2016

(87) PCT Pub. No.: WO2015/071235
PCT Pub. Date: May 21, 2015

(65) Prior Publication Data
US 2016/0264525 A1    Sep. 15, 2016

(30) Foreign Application Priority Data
Nov. 13, 2013 (GB) .................................. 1320021.7

(51) Int. Cl.
*C07D 211/54* (2006.01)
*A61K 31/4462* (2006.01)

(52) U.S. Cl.
CPC ........ *C07D 211/54* (2013.01); *A61K 31/4462* (2013.01)

(58) Field of Classification Search
None
See application file for complete search history.

(56) References Cited

U.S. PATENT DOCUMENTS 7,893,089 B2 *   2/2011   Busch-Petersen ... C07D 205/04
                                                      514/317

FOREIGN PATENT DOCUMENTS

WO    2007/124424 A2    11/2007

OTHER PUBLICATIONS

Pandit "Introduction to the pharmaceutical sciences" 2006, Lippincott, Williams and Wilkins: Baltimore, p. 19.*
Stahl "Handbook of Pharmaceutical Salts: Properties Selection and Use" Verlag Helvetica Chimica Acta: 2002, pp. 118-121 220-235, 288-289.*
Paulekuhn "Trends in Active Pharmaceutical Ingredient Salt Selection based on Analysis of the Orange Book Database" Journal of Medicinal Chemistry 2007, 50, 6665-6672.*
West, Anthony R., "Solid State Chemistry and its Applications", Wiley, New York, 1988, pp. 358 & 365.*
Berge, S.M., et al. Pharmaceutical Salts. Journal of Pharrnaceuticai Sciences, American Pharmaceutical Association, vol. 66, No. 1, Jan. 1, 1977, pp. 1-19.
Bloomer, J.C., et al. Assessment of Potential Drug Interactions by Characterization of Human Drug Metabolism Pathways, Using Non-Invasive Biie Sampling. British Journal of Clinical Pharmacology, vol. 75, No. 2, Feb. 10, 2013, pp. 488-496.
Bloomer, et al., Identification and characterisation of a salt form of Danirixin with reduced pharmacokinetic variability in patient populations, European Journal of Pharmaceutics and Biopharmaceutics, vol. 117, pp. 224-231, 2017.

* cited by examiner

*Primary Examiner* — David K O'Dell
(74) *Attorney, Agent, or Firm* — Fang Qian

(57) ABSTRACT

A compound which is the hydrobromide salt of N-{4-chloro-2-hydroxy-3-[(3S)-3-piperidinylsulfonyl]phenyl}-N'-(3-fluoro-2-methylphenyl)urea, compositions, combinations and medicaments containing said compounds and processes for their preparation. The invention also relates to the use of said compounds, combinations, compositions and medicaments.

6 Claims, 2 Drawing Sheets

Figure 1:
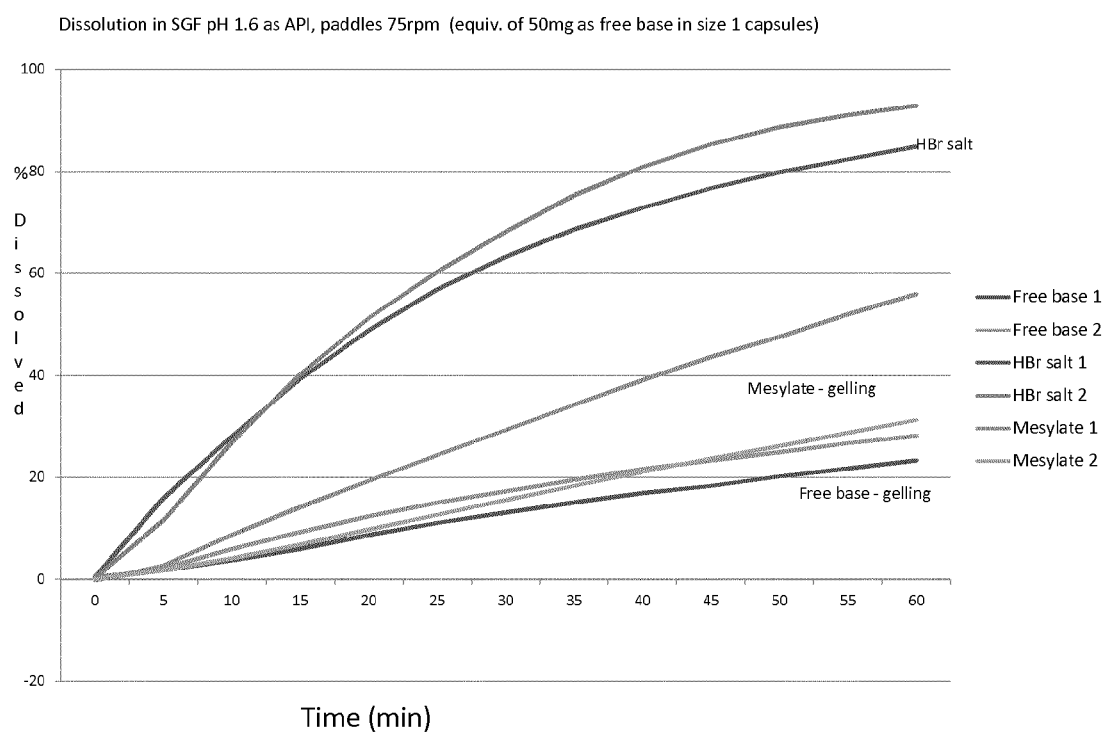

FIGURE 2 HBr salt drug provides the greatest rate of dissolution at an elevated gastric pH
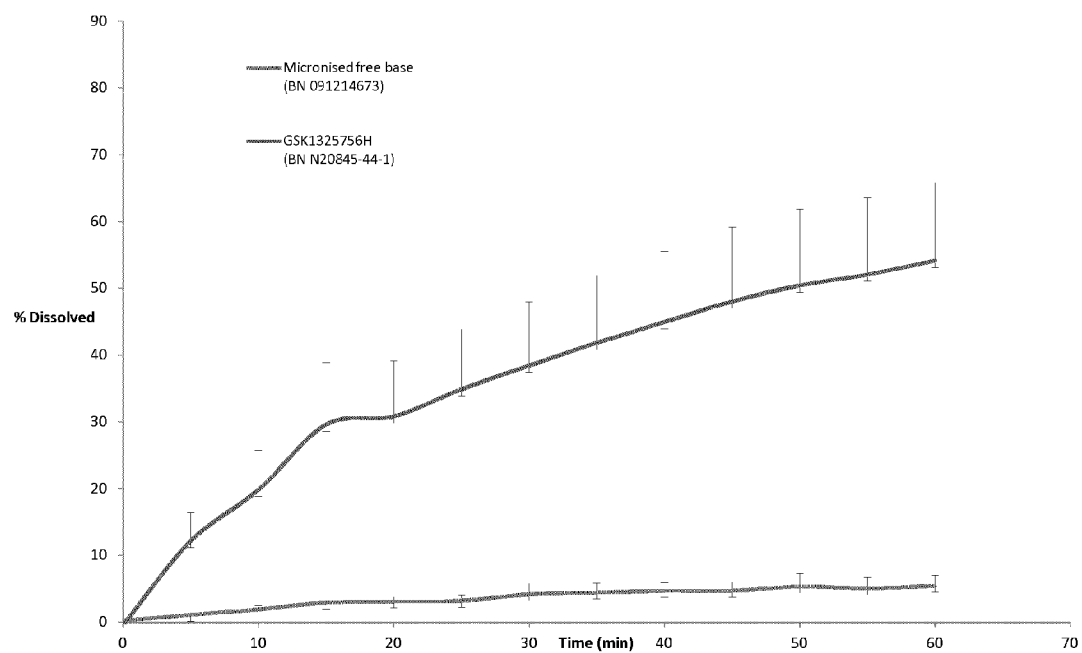

HYDROBROMIDE SALT OF N-(4-CHLORO-2-HYDROXY-3-((3S)-3-PIPERIDINYLSULFONYL)PHENYL-N'-(3-FLUORO-2-METHYLPHENYL)UREA

CROSS-REFERENCE TO RELATED APPLICATIONS

This application is filed pursuant to 35 USC 371 as a United States National Phase Application of International Patent Application Serial No. PCT/EP2014/074222 filed on Nov. 1, 2014, which claims priority from 1320021.7 filed on Nov. 13, 2013, in the United Kingdom.

FIELD OF THE INVENTION

The present invention relates to a novel hydrobromide salt of N-{4-chloro-2-hydroxy-3-[(3S)-3-piperidinylsulfonyl]phenyl}-N'-(3-fluoro-2-methylphenyl)urea, compositions, combinations and medicaments containing said compounds and processes for its preparation. The invention also relates to the use of said compounds, combinations, compositions and medicaments in treating disease or conditions for which a CXCR2 antagonist is indicated.

BACKGROUND OF THE INVENTION

CXCR2 is a well-characterized G-protein coupled receptor for a number of chemokines that share the Glu-Leu-Arg (ELR) motif including interleukin-8 (IL-8, CXCL8) and growth regulated oncogene alpha, beta and gamma, (GROα, β,γ or CXCL1,2,3) that are known to be involved in the recruitment of neutrophils to a site of injury [Reutershan, J. (2006) Drug News Perspect 19:615-623]. CXCR2 is expressed primarily on neutrophils (PMN), but can be expressed on other leukocytes as well such as monocytes. Antagonism of CXCR2 has been shown to be effective in blocking the recruitment of PMN to the lung in response to stimuli such as LPS, cigarette smoke, or ozone exposure both preclinically and in humans [Thatcher T H (2005) Am Jour Phys Lung Cell Mol Phys 289:L322-L328; Reutershan J (2006) J Clin Invest 116:695-702]. Holz O, Khalilieh S, Ludwig-Sengpiel A, Watz H, Stryszak P, Soni P, Tsai M, Sadeh J, Magnussen H. SCH527123, a novel CXCR2 antagonist, inhibits ozone-induced neutrophilia in healthy subjects. Eur Respir J 2010; 35:564-570 Lazaar A L, Sweeney L E, MacDonald A J, Alexis N E, Chen C, Tal-Singer R. SB-656933, a novel CXCR2 selective antagonist, inhibits ex vivo neutrophil activation and ozone-induced airway inflammation in humans. Br. J. Clin. Pharmacol. 72:282-293 (2011) Selective antagonism of the interaction between CXCR2 and its various chemokine ligands provides a potential strategy for reducing the underlying inflammation that contributes to the progression of multiple diseases [Chapman R W, Phillipsa J E, Hipkina R W, Currana A K, Lundella D and Fine J S. CXCR2 antagonists for the treatment of pulmonary disease. Pharmacol. Ther. 2009; 121(1): 55-68. as demonstrated in preliminary studies in patients with respiratory diseases (Nair P, Gaga M, Zervas E, Alagha K, Hargreave F E, O'Byrne P M, Stryszak P, Gann L, Sadeh J, Chanez P; Study Investigators. Safety and efficacy of a CXCR2 antagonist in patients with severe asthma and sputum neutrophils: a randomized, placebo-controlled clinical trial. Clin Exp Allergy 2012; 42:1097-2103) Rennard S I, Dale D C, Donohure J F, Kanniess F, Magnussen H, Sutherland E R, Watz H, Lu S, Stryszak P, Rosenberg E, Staudinger H. CXCR2 antagonist MK-7123—a phase 2 proof-of-concept trial for chronic obstructive pulmonary disease. Am J Respir Crit Care Med 2013; 187:A6071.

The CXC chemokines that possess the ELR motif (e.g., CXCL1/GROα, CXCL8/IL-8) are important in the recruitment of inflammatory cells that mediates pathology in multiple organ settings. Pathology is related, for example, to inappropriately released hydrolytic enzymes and reactive oxygen species from activated neutrophils. On the other hand, during most bacterial infections this chemokine response represents a critical first line of defense, but even here $ELR^+$ CXC chemokine responses can, via their abilities to activate inflammatory cells displaying the CXCR1 and CXCR2 receptors, exacerbate the pathology. Despite the critical importance of these chemokine responses in many settings, inflammatory cell responses are sufficiently damaging that identification of therapeutic tools to block $ELR^+$ chemokines is of interest.

The ELR chemokines chemoattract and activate inflammatory cells via their CXCR1 and CXCR2 receptors. The CXCR1 is specific for CXCL8 and CXCL6, while the CXCR2 binds CXCL8 with high affinity, but also binds CXCL1, CXCL5 and CXCL6 with somewhat lower affinities. CXCL8 signaling in cell lines transfected with the human CXCR1 or CXCR2 induces equipotent chemotactic responses. Neutrophil cytosolic free $Ca^{++}$ changes and cellular degranulation in response to CXCL8 are also mediated by both receptors, but the respiratory burst and activation of phospholipase D reportedly depend exclusively on CXCR1. On the other hand, it has been reported that a non-peptide antagonist of CXCR2, but not CXCR1, antagonizes CXCL8-mediated neutrophil chemotaxis, but not cellular activation. Finally, there is abundant evidence that chemokines are most often redundantly expressed during inflammatory responses.

WO 2007/124424 discloses compounds useful in the treatment of disease states mediated by IL-8, including the compound N-{4-chloro-2-hydroxy-3-[3-piperidinylsulfonyl]phenyl}-N'-(3-fluoro-2-methylphenyl)urea, and the enantiomer N-{4-chloro-2-hydroxy-3-[(3S)-3-piperidinylsulfonyl]phenyl}-N'-(3-fluoro-2-methylphenyl) urea.

There remains a need for treatment, in this field, for compounds which are capable of antagonising CXCR2.

SUMMARY OF THE INVENTION

In one aspect there is provided a novel hydrobromide salt of N-{4-chloro-2-hydroxy-3-[-3-piperidinylsulfonyl]phenyl}-N'-(3-fluoro-2-methylphenyl)urea, particularly the hydrobromide salt of the enantiomer N-{4-chloro-2-hydroxy-3-[(3S)-3-piperidinylsulfonyl]phenyl}-N'-(3-fluoro-2-methylphenyl)urea (the present compound).

In a further aspect of the present invention, there is provided the present compound for use in therapy, in particular in the treatment of a disease or condition for which a CXCR2 antagonist is indicated.

In a further aspect of the present invention, there is provided a pharmaceutical composition comprising the present compound and one or more of pharmaceutically acceptable carriers, diluents and excipients.

In a further aspect of the present invention, there is provided a method of treating a disease or condition for which a CXCR2 antagonist is indicated comprising administering a therapeutically effective amount of the present compound.

In a further aspect of the present invention, there is provided the use of the present compound in the manufacture of a medicament for use in treating a disease or condition for which a CXCR2 antagonist is indicated.

In a further aspect there is provided a combination comprising the present compound and at least one further therapeutic agent.

In a further aspect there is provided a pharmaceutical composition comprising the present compound and at least one further therapeutic agent and one or more of pharmaceutically acceptable carrier, diluents and excipients.

In a further aspect there is provided a combination comprising the present compound and at least one further therapeutic agent for use in therapy, particularly for treating a disease or condition for which a CXCR2 antagonist is indicated.

In a further aspect there is provided a method of treating a disease or condition for which a CXCR2 antagonist is indicated comprising administering to a human in need thereof a therapeutically effective amount of a combination comprising the present compound and at least one further therapeutic agent.

In a further aspect there is provided the use of a combination comprising the present compound and at least one further therapeutic agent in the manufacture of a medicament for treating a disease or condition for which a CXCR2 antagonist is indicated.

In a further aspect there is provided a method of inhibiting the binding of IL 8 to its receptors in a mammal, particularly a human which comprises administering a therapeutically effective amount of the present compound.

LIST OF FIGURES

FIG. 1: HBr salt presents enhanced dissolution rate without gelling at low gastric pH FIG. 2: HBr salt provides the greatest rate of dissolution at an elevated gastric pH.

DETAILED DESCRIPTION OF THE INVENTION

It is found that the hydrobromide salt demonstrates advantages over the free base which makes it particularly suitable for use in treating diseases or conditions for which a CXCR2 antagonist is indicated, for example, chronic obstructive pulmonary disease (COPD).

Specifically, the hydrobromide salt demonstrates improved solubility and dissolution profiles at higher pH as compared to the free base. Many COPD patients also take proton pump inhibitors and thus can have a higher than average gastric pH. Such patients would not receive the same exposure to the free base as otherwise healthy patients and therefore the increased solubility and dissolution of the hydrobromide salt increases exposure in such patients.

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The present compound may exist in solvated and unsolvated forms. As used herein, the term "solvate" refers to a complex of variable stoichiometry formed by a solute (in this invention, a compound of formula (I) or a salt) and a solvent. Such solvents for the purpose of the invention may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice incorporated with water molecules are typically referred to as "hydrates". Hydrates include stoichiometric hydrates as well as compositions containing variable amounts of water. In one embodiment, the present compound is a hemihydrate.

The present compound may have the ability to crystallize in more than one form, a characteristic, which is known as polymorphism, and it is understood that such polymorphic forms ("polymorphs") are within the scope of the invention. Polymorphism generally can occur as a response to changes in temperature or pressure or both and can also result from variations in the crystallization process. Polymorphs can be distinguished by various physical characteristics known in the art such as x-ray diffraction patterns, solubility and melting point.

While it is possible that, for use in therapy, the present compound may be administered as the raw chemical, it is possible to present the active ingredient as a pharmaceutical composition. Accordingly, the invention further provides pharmaceutical compositions comprising the present compound and one or more pharmaceutically acceptable carriers, diluents, or excipients. The carrier(s), diluents(s) or excipient(s) must be acceptable in the sense of being compatible with the other ingredients of the composition and not deleterious to the recipient thereof. In accordance with another aspect of the invention there is also provided a process for the preparation of a pharmaceutical composition including the agent, or pharmaceutically acceptable salts thereof, with one or more pharmaceutically acceptable carriers, diluents or excipients. The pharmaceutical composition can be for use in the treatment and/or prophylaxis of any of the conditions described herein.

Pharmaceutical compositions may be presented in unit dose forms containing a predetermined amount of active ingredient per unit dose. Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Pharmaceutical compositions may be adapted for administration by any appropriate route, for example by the oral (including buccal or sublingual), rectal, inhaled, intranasal, topical (including buccal, sublingual or transdermal), vaginal or parenteral (including subcutaneous, intramuscular, intravenous or intradermal) route. Such compositions may be prepared by any method known in the art of pharmacy, for example by bringing into association the active ingredient with the carrier(s) or excipient(s).

Pharmaceutical compositions adapted for oral administration may be presented as discrete units such as capsules or tablets; powders or granules; solutions or suspensions in aqueous or non-aqueous liquids; edible foams or whips; or oil-in-water liquid emulsions or water-in-oil liquid emulsions.

For instance, for oral administration in the form of a tablet or capsule, the active drug component can be combined with an oral, non-toxic pharmaceutically acceptable inert carrier such as ethanol, glycerol, water and the like. Powders are prepared by reducing the compound to a suitable fine size and mixing with a similarly prepared pharmaceutical carrier such as an edible carbohydrate, as, for example, starch or mannitol. Flavouring, preservative, dispersing and colouring agent can also be present.

Capsules are made by preparing a powder mixture, as described above, and filling formed gelatin sheaths. Glidants and lubricants such as colloidal silica, talc, magnesium stearate, calcium stearate or solid polyethylene glycol can be added to the powder mixture before the filling operation. A disintegrating or solubilizing agent such as agar-agar, calcium carbonate or sodium carbonate can also be added to improve the availability of the medicament when the capsule is ingested.

Moreover, when desired or necessary, suitable binders, glidants, lubricants, sweetening agents, flavours, disintegrating agents and colouring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder such as carboxymethylcellulose, an aliginate, gelatin, or polyvinyl pyrrolidone, a solution retardant such as paraffin, a resorption accelerator such as a quaternary salt and/or an absorption agent such as bentonite, kaolin or dicalcium phosphate. The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present invention can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

As used herein, the present compound includes all solvates, complexes, polymorphs, radiolabelled derivatives, of the hydrobromide salt of N-{4-chloro-2-hydroxy-3-[(3S)-3-piperidinylsulfonyl]phenyl}-N'-(3-fluoro-2-methylphenyl) urea.

Oral fluids such as solution, syrups and elixirs can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Where appropriate, dosage unit compositions for oral administration can be microencapsulated. The composition can also be prepared to prolong or sustain the release as for example by coating or embedding particulate material in polymers, wax or the like.

The compounds of the invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Pharmaceutical compositions adapted for transdermal administration may be presented as discrete patches intended to remain in intimate contact with the epidermis of the recipient for a prolonged period of time.

Pharmaceutical compositions adapted for topical administration may be formulated as ointments, creams, suspensions, lotions, powders, solutions, pastes, gels, sprays, aerosols or oils.

For treatments of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base.

Pharmaceutical compositions adapted for topical administrations to the eye include eye drops wherein the active ingredient is dissolved or suspended in a suitable carrier, especially an aqueous solvent.

Pharmaceutical compositions adapted for topical administration in the mouth include lozenges, pastilles and mouth washes.

Pharmaceutical compositions adapted for rectal administration may be presented as suppositories or as enemas.

Dosage forms for nasal or inhaled administration may conveniently be formulated as aerosols, solutions, suspensions drops, gels or dry powders.

Pharmaceutical compositions adapted for vaginal administration may be presented as pessaries, tampons, creams, gels, pastes, foams or spray formulations.

Pharmaceutical compositions adapted for parental administration include aqueous and non-aqueous sterile injection solutions which may contain anti-oxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

It should be understood that in addition to the ingredients particularly mentioned above, the compositions may include other agents conventional in the art having regard to the type of formulation in question, for example those suitable for oral administration may include flavouring agents.

A therapeutically effective amount of the present compound will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or in a number (such as two, three, four, five or six) of sub-doses per day such that the total daily dose is the same.

For all methods of use disclosed herein for the compound of the invention the daily oral dosage regimen will preferably be from about 0.01 to about 80 mg/kg of total body weight. The daily parenteral dosage regimen about 0.001 to about 80 mg/kg of total body weight. The daily topical dosage regimen will preferably be from 0.1 mg to 150 mg, administered one to four, preferably two or three times daily. The daily inhalation dosage regimen will preferably be from about 0.01 mg/kg to about 1 mg/kg per day. It will also be recognized by one of skill in the art that the optimal quantity and spacing of individual dosages of a compound of the invention will be determined by the nature and extent of the condition being treated, the form, route and site of administration, and the particular patient being treated, and that such optimums can be determined by conventional techniques. It will also be appreciated by one of skill in the art that the optimal course of treatment, i.e., the number of doses of a compound of the invention given per day for a defined number of days, can be ascertained by those skilled in the art using conventional course of treatment determination tests. All the above relate to amounts of the free base.

The present compound is useful in the manufacture of a medicine for the prophylactic or therapeutic treatment of any disease state in a human, or other mammal, for which a CXCR2 antagonist is indicated.

Accordingly, the present invention provides a method of treating a disease or condition for which a CXCR2 antagonist is indicated and which method comprises administering an effective amount of the present compound.

There are many disease states in which a CXCR2 antagonist is indicated. Chemokine mediated diseases include psoriasis, atopic dermatitis, osteo arthritis, rheumatoid arthritis, asthma, chronic obstructive pulmonary disease, adult respiratory distress syndrome, inflammatory bowel disease, Crohn's disease, ulcerative colitis, stroke, septic shock, endotoxic shock, gram negative sepsis, toxic shock syndrome, cardiac and renal reperfusion injury, glomerulonephritis, thrombosis, graft vs. host reaction, alzheimers disease, allograft rejections, malaria, restinosis, angiogenesis, atherosclerosis, osteoporosis, gingivitis, viral diseases such as rhinovirus or undesired hematopoietic stem cell release. In particular, the compound of the present invention is useful in the treatment of asthma, chronic obstructive pulmonary disease and adult respiratory distress syndrome. Preferably, the present compound is useful for treating chronic obstructive pulmonary disease.

The diseases of the present invention are primarily characterized by massive neutrophil infiltration, T-cell infiltration, or neovascular growth, and are associated with increased IL-8, GROα, GROβ, GROγ, NAP-2 or ENA-78 production which is responsible for the chemotaxis of neutrophils into the inflammatory site or the directional growth of endothelial cells. In contrast to other inflammatory cytokines (IL-1, TNF, and IL-6), IL-8, GROα, GROβ, GROγ, NAP-2 or ENA-78 have the unique property of promoting neutrophil chemotaxis, enzyme release including but not limited to elastase release as well as superoxide production and activation. The a-chemokines, but particularly, GROα, GROβ, GROγ, NAP-2 or ENA-78, working through the IL-8 type I or II receptor, can promote the neovascularization of tumors by promoting the directional growth of endothelial cells. Therefore, the inhibition of IL-8 induced chemotaxis or activation would lead to a direct reduction in the neutrophil infiltration. Recent evidence also implicates the role of chemokines in the treatment of HIV infections, Littleman et al., Nature 381, pp. 661 (1996) and Koup et al., Nature 381, pp. 30 667 (1996).

Present evidence also indicates the use of IL-8 inhibitors in the treatment of atherosclerosis. The first reference, Boisvert et al., 1. Clin. Invest, 1998, 101:353-363 shows, through bone marrow transplantation, that the absence of IL-8 receptors on stem cells (and, therefore, on monocytes/macrophages) leads to a reduction in the development of atherosclerotic plaques in LDL receptor deficient mice.

The present invention also provides for a means of treating CNS injuries. Such treatment is provided in an acute setting, as well as for prevention of injury in those individuals deemed susceptible to injury. CNS injuries as defined herein include both open or penetrating head trauma, such as by surgery, or a closed head trauma injury, such as by an injury to the head region. Also included within this definition is ischemic stroke, particularly to the brain area. Ischemic stroke may be defined as a focal neurologic disorder that results from insufficient blood supply to a particular brain area, usually as a consequence of an embolus, thrombi, or local atheromatous closure of the blood vessel. The role of inflammatory cytokines in this area has been emerging and the present invention provides means for the potential treatment of these injuries. Relatively little treatment, for an acute injury such as these has been available.

TNF-a is a cytokine with proinflammatory actions, including endothelial leukocyte adhesion molecule expression. Leukocytes infiltrate into ischemic brain lesions and hence compounds which inhibit or decrease levels of TNF would be useful for treatment of ischemic brain injury. See Liu et al., Stroke, Vol. 25., No. 7, pp. 1481-88 (1994) whose disclosure is incorporated herein by reference.

Models of closed head injuries and treatment with mixed 5-LOICO agents is discussed in Shohami et al., 1. of Vaisc & Clinical Physiology and Pharmacology, Vol. 3, No. 2, pp. 99-107 (1992). Treatment which reduced edema formation was found to improve functional outcome in those animals treated.

As used herein, the term "cytokine" refers to any secreted polypeptide that affects the functions of cells and is a molecule which modulates interactions between cells in the immune, inflammatory or hematopoietic response. A cytokine includes, but is not limited to, monokines and lymphokines, regardless of which cells produce them. For instance, a monokine is generally referred to as being produced and secreted by a mononuclear cell, such as a macrophage and/or monocyte. Many other cells however also produce monokines, such as natural killer cells, fibroblasts, basophils, neutrophils, endothelial cells, brain astrocytes, bone marrow stromal cells, epideral keratinocytes and B-lymphocytes.

The compounds of the present invention may be used in combination with or include one or more other therapeutic agents and may be administered either sequentially or simultaneously by any convenient route in separate or combined pharmaceutical compositions.

Thus the invention includes in a further aspect a combination comprising a the present compound together with at least one other therapeutically active agent.

The amounts of the compound(s) of the invention and the other pharmaceutically active agent(s) and the relative timings of administration will be selected in order to achieve the desired combined therapeutic effect.

The compounds of the present invention and further therapeutic agent(s) may be employed in combination by administration simultaneously in a unitary pharmaceutical composition including both compounds. Alternatively, the combination may be administered separately in separate pharmaceutical compositions, each including one of the compounds in a sequential manner wherein, for example, the compound of the invention is administered first and the other second and vice versa. Such sequential administration may be close in time (e.g. simultaneously) or remote in time. Furthermore, it does not matter if the compounds are administered in the same dosage form, e.g. one compound may be administered topically and the other compound may be administered orally.

The combinations may be presented as a combination kit. By the term "combination kit" "or kit of parts" as used herein is meant the pharmaceutical composition or compositions that are used to administer the combination according to the invention. When both compounds are administered simultaneously, the combination kit can contain both compounds in a single pharmaceutical composition, such as a tablet, or in separate pharmaceutical compositions. When the compounds are not administered simultaneously, the combination kit will contain each compound in separate pharmaceutical compositions either in a single package or in separate pharmaceutical compositions in separate packages.

The combination kit can also be provided by instruction, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited, For example, one agent may be administered once a day, and the other agent may be administered 2 or 3 times a day, or one agent may be administered once a week, and the other agent may be administered once a day and the like.

It will be clear to a person skilled in the art that, where appropriate, the other therapeutic ingredients(s) may be used in the form of salts, for example as alkali metal or amine salts or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

When combined in the same composition it will be appreciated that the two compounds must be stable and compatible with each other and the other components of the composition and may be formulated for administration. When formulated separately they may be provided in any convenient composition, conveniently, in such a manner as known for such compounds in the art.

When the compound of the invention is used in combination with a second therapeutic agent active against the same disease, condition or disorder, the dose of each compound may differ from that when the compound is used alone. Appropriate doses will be readily appreciated by those skilled in the art.

The present compound may be used in combination with one or more other agents which may be useful in the prevention or treatment of allergic disease, inflammatory disease, autoimmune disease, for example; antigen immunotherapy, anti-histamines, corticosteroids (eg fluticasone propionate, fluticasone furoate, beclomethasone diproprionate, budesonide, ciclesonide, mometasone furoate, triamcinolone, flunisolide), NSAIDs, leukotriene modulators (e.g. montelukast, zafirlukast, pranlukast) iNOS inhibitors, tryptase inhibitors, IKK2 inhibitors, p38 inhibitors, Syk inhibitors, elastase inhibitors, beta-2 integrin antagonists, adenosine ata agonists, chemokine antagonists such as CCR3 antagonists or CCR4 antagonists, mediator release inhibitors such as sodium chromoglycate, 5-lipoxygenase inhibitors (zyflo), DP1 antagonists, DP2 antagonists, pI3K delta inhibitors, ITK inhibitors, LP (lysophosphatidic) inhibitors or FLAP (5-lipoxygenase activating protein) inhibitors (e.g. sodium 3-(3-(tert-butylthio)-1-(4-(6-ethoxypyridin-3-yl)benzyl)-5-((5-methylpyridin-2-yl)methoxy)-1H-indol-2-yl)-2,2-dimethylpropanoate), bronchodilators (e.g. beta-2 agonists, adrenergic agonists, anticholinergic agents, theophylline), methotrexate, and similar agents; monoclonal antibody therapy such as anti-IgE, anti-TNF, anti-IL-5, anti-IL-6, anti-IL-12, anti-IL-1 and similar agents; receptor therapies e.g. etanercept and similar agents; antigen non-specific immunotherapies (e.g. interferon or other cytokines/chemokines, cytokine/chemokine receptor modulators, cytokine agonists or antagonists, TLR agonists and similar agents).

The present compound may be prepared by methods known in the art of organic synthesis as set forth in the specific Examples described below. In all of the methods, it is well understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, $3^{rd}$ edition, John Wiley & Sons). These groups are removed at a convenient stage of the compound synthesis using methods that are readily apparent to those skilled in the art. The selection of processes as well as the reaction conditions and order of their execution shall be consistent with the preparation of the compounds of the invention.

EXPERIMENTAL

Synthesis of the hydrobromide salt of N-{4-chloro-2-hydroxy-3-[(3S)-3-piperidinylsulfonyl]phenyl}-N'-(3-fluoro-2-methylphenyl) urea

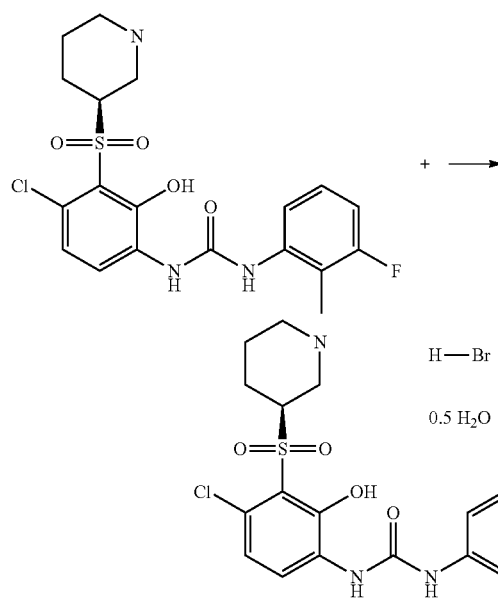

N-{4-chloro-2-hydroxy-3-[(3S)-3-piperidinylsulfonyl]phenyl}-N'-(3-fluoro-2-methylphenyl) urea (which may be prepared as described in WO2007/124424) was slurried in IPA at 50±3° C. before 48 wt % HBr in water was added over at least 30 mins and washed in with water. The reaction mixture was aged at 50±3° C. for at least 180 mins before being heated to 75±3° C. The resulting solution was clarified into a clean vessel followed by 10 wt % water in IPA at 75±3° C. The resulting solution was cooled to 40±3° C. before being seeded with the hydrobromide salt, slurried in 10 wt % water in IPA which had been sonicated for at least 2 mins. The resulting slurry was then aged at 40±3° C. for at least 48 hrs before being cooled to 0±3° C. at 0.2° C. per min. The resulting slurry was aged at 0±3° C. for at least 24 hrs before the solid is collected by filtration and washed with 10 wt % water in IPA. The seed was prepared by adding cHBr to a slurry of the free base compound in IPA, which was then used to seed subsequent and larger batches.

The product was dried under vacuum at 50±5° C. The HBr salt is a hemihydrate

Solubility

The solubility of the HBr salt is higher than the free base at higher pH's and in simulated intestinal fluids (see tables below). The solubility in simulated intestinal fluids does reduce with time but is still much higher than the equivalent free base solubility.

| Media | Solubility (mcg/ml) | | | | | |
|---|---|---|---|---|---|---|
| | Micronised free base | | | HBr Salt | | |
| | 0.5 hr | 4 hr | 24 hr | 0.5 hr | 4 hr | 24 hr |
| SGF pH1.6 | 715 | 808 | 842 | 757 | 795 | 779 |
| Phares FaSSIF pH 6.5 | 9 | 18 | 10 | 459 | 272 | 56 |
| Phares FeSSIF pH 6.5 | 19 | 24 | 25 | 724 | 841 | 340 |
| pH 2.0 | 601 | 662 | 697 | 605 | 635 | 609 |
| pH 4.0 | 21 | 23 | 24 | 685 | 670 | 609 |
| pH 6.0 | 4 | 4 | 4 | 194 | 13 | 5 |
| pH 8.0 | 5 | 5 | 5 | 52 | 13 | 8 |

| Media | HBr Salt—Solubility (mcg/ml) | | | | | | | | |
|---|---|---|---|---|---|---|---|---|---|
| | Batch 1 | | | Batch 2 | | | Batch 3 | | |
| | 0.5 hr | 4 hr | 24 hr | 0.5 hr | 4 hr | 24 hr | 0.5 hr | 4 hr | 24 hr |
| SGF pH 1.6 | 770 | 787 | 795 | 414 | 647 | 800 | 757 | 795 | 779 |
| Phares FaSSif pH 6.5 | 420 | 384 | 64 | 270 | 379 | 79 | 459 | 227 | 56 |
| Phares FeSSIF pH .5 | 838 | 833 | 788 | 478 | 846 | 834 | 724 | 841 | 340 |
| pH 2.0 | NT | NT | NT | NT | NT | NT | 605 | 635 | 609 |
| pH 4.0 | NT | NT | NT | NT | NT | NT | 685 | 670 | 609 |
| pH 6.0 | NT | NT | NT | NT | NT | NT | 194 | 13 | 5 |
| pH 8.0 | NT | NT | NT | NT | NT | NT | 52 | 13 | 8 |

Dissolution

Dissolution profiles of the HBr salt (50 mg as free form) in a capsule compared with the free base in pH1.6 simulated gastric fluid and in pH 4 citrate buffer. The HBr salt is better. The mesylate appeared to gel and HBr was considered superior to both the mesylate salt and the free base. See FIGS. 1 and 2.

What is claimed is:

1. A compound which is a hemihydrate of the hydrobromide salt of N-{4-chloro-2-hydroxy-3-[(3S)-3-piperidinylsulfonyl]phenyl}-N'-(3-fluoro-2-methylphenyl)urea.

2. A pharmaceutical composition comprising a compound of claim 1 and one or more of pharmaceutically acceptable carriers, diluents and excipients.

3. A method of treating COPD in a subject comprising administering a therapeutically effective amount of a compound of according to claim 1.

4. A combination comprising a compound according to claim 1 and at least one further therapeutic agent.

5. A method of treating COPD comprising administering to a human in need thereof a therapeutically effective amount of a combination according to claim 3.

6. A pharmaceutical composition comprising a combination according to claim 4 and one or more of pharmaceutically acceptable carriers, diluents and excipients.

* * * * *

UNITED STATES PATENT AND TRADEMARK OFFICE
CERTIFICATE OF CORRECTION

PATENT NO. : 9,809,540 B2  
APPLICATION NO. : 15/034583  
DATED : November 7, 2017  
INVENTOR(S) : Francis Dominic Sanderson and Sarah Mary Vallance Page 1 of 1

It is certified that error appears in the above-identified patent and that said Letters Patent is hereby corrected as shown below:

On the Title Page

Item (54) and in the Specification, Column 1, Line 1, Title: please replace "N-(4-CHLORO-2-HYDROXY-3-((3S)-3-PIPERIDINYLSULFONYL)PHENYL-N'-(3-FLUORO-2-METHYLPHENYL)UREA" with -- N-(4-CHLORO-2-HYDROXY-3-((3S)-3-PIPERIDINYLSULFONYL)PHENYL)-N'-(3-FLUORO-2-METHYLPHENYL)UREA --;

In the Claims

Column 12, Lines 48-49, Claim 3: please replace "a compound of according to claim 1" with -- a compound according to claim 1 --;

Column 12, Line 54, Claim 5: please replace "a combination according to claim 3" with -- a combination according to claim 4 --.

Signed and Sealed this  
Seventh Day of April, 2020

Andrei Iancu  
*Director of the United States Patent and Trademark Office*